(12) United States Patent
Hopkins et al.

(10) Patent No.: US 8,946,500 B2
(45) Date of Patent: Feb. 3, 2015

(54) ABSORBENT ARTICLE WITH HIGHLIGHTED PASSIVE BARRIER

(75) Inventors: Heidi Bauerlein Hopkins, Neenah, WI (US); Adrienne Rae Loyd, Neenah, WI (US); Ramona Zenkich, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 225 days.

(21) Appl. No.: 13/599,062

(22) Filed: Aug. 30, 2012

(65) Prior Publication Data

US 2014/0066875 A1 Mar. 6, 2014

(51) Int. Cl.
*A61F 13/15* (2006.01)

(52) U.S. Cl.
USPC .......................................................... 604/361

(58) Field of Classification Search
CPC ........... A61F 13/47218; A61F 13/4751; A61F 13/4752; A61F 13/4753; A61F 2103/8497
USPC .......................................................... 604/361
See application file for complete search history.

(56) References Cited

U.S. PATENT DOCUMENTS

| | | | |
|---|---|---|---|
| 4,623,340 A * | 11/1986 | Luceri | 604/385.05 |
| 4,834,733 A | 5/1989 | Huntoon et al. | |
| 5,897,541 A | 4/1999 | Uitenbroek | |
| 6,719,742 B1 * | 4/2004 | McCormack et al. | 604/385.01 |
| D542,410 S | 5/2007 | Jackson | |
| D542,412 S | 5/2007 | Gubernick | |
| D571,004 S | 6/2008 | Georgi | |
| 7,432,412 B2 * | 10/2008 | Kigata et al. | 604/367 |
| D600,798 S | 9/2009 | Denti | |
| D600,799 S | 9/2009 | Larson | |
| D600,800 S | 9/2009 | Denti | |
| D600,801 S | 9/2009 | Larson | |
| D600,802 S | 9/2009 | Denti | |
| D600,803 S | 9/2009 | Larson | |
| D612,491 S | 3/2010 | Zunker | |
| 7,863,497 B2 * | 1/2011 | Magee et al. | 604/361 |
| D636,076 S | 4/2011 | Denti | |
| D639,422 S | 6/2011 | Rave | |
| D641,867 S | 7/2011 | Hood | |
| 8,324,444 B2 * | 12/2012 | Hansson et al. | 604/361 |
| 2002/0004654 A1 | 1/2002 | Bruce | |
| 2002/0143312 A1 | 10/2002 | Graeme, III | |

(Continued)

FOREIGN PATENT DOCUMENTS

| | | |
|---|---|---|
| EP | 2 250 984 A1 | 11/2010 |
| JP | 2006-239162 A2 | 9/2006 |

(Continued)

*Primary Examiner* — Lynne Anderson
(74) *Attorney, Agent, or Firm* — Kimberly-Clark Worldwide, Inc.

(57) ABSTRACT

An absorbent article includes an absorbent core, a garment-facing surface, a body-facing surface, a first graphic visible at the body-facing surface, and a top component affixed to the article body and including an attached region and a cantilevered region, wherein the cantilevered region includes a translucent portion through which the first graphic is at least partially visible. The translucent portion can include a second graphic, wherein the first graphic and the second graphic combine to form the appearance of a third graphic. The article can also include a baffle forming at least part of the garment-facing surface, wherein the baffle includes a baffle graphic, and wherein at least a portion of the article body is translucent such that the baffle graphic is visible at the body-facing surface such that the first graphic and the baffle graphic combine to form the appearance of a fourth graphic.

19 Claims, 5 Drawing Sheets

(56) References Cited

U.S. PATENT DOCUMENTS

| | | |
|---|---|---|
| 2003/0065299 A1 | 4/2003 | Gagliardi |
| 2003/0109839 A1 | 6/2003 | Pretz |
| 2003/0114811 A1 | 6/2003 | Feller |
| 2003/0149410 A1 | 8/2003 | Kudo et al. |
| 2004/0015145 A1 | 1/2004 | Sasaki |
| 2004/0233241 A1 | 11/2004 | Salacz |
| 2005/0101931 A1 | 5/2005 | Alcantara |
| 2006/0004333 A1* | 1/2006 | Olson .......................... 604/361 |
| 2006/0111684 A1 | 5/2006 | Arora |
| 2007/0087169 A1 | 4/2007 | Mcfall |
| 2008/0065037 A1 | 3/2008 | Konawa |
| 2008/0294139 A1 | 11/2008 | Ecker |
| 2008/0294140 A1 | 11/2008 | Ecker |
| 2008/0300560 A1* | 12/2008 | Magnusson et al. .......... 604/367 |
| 2009/0012491 A1 | 1/2009 | Addario |
| 2009/0157021 A1 | 6/2009 | Woltman |
| 2009/0281513 A1 | 11/2009 | Nelson |
| 2010/0082008 A1 | 4/2010 | Veglio |
| 2010/0152692 A1 | 6/2010 | Ong et al. |
| 2010/0191209 A1 | 7/2010 | Nomoto et al. |
| 2011/0270208 A1 | 11/2011 | Miura et al. |
| 2012/0143163 A1 | 6/2012 | Ng |
| 2012/0157949 A1 | 6/2012 | Knight et al. |
| 2012/0296303 A1 | 11/2012 | Ng et al. |
| 2012/0296304 A1 | 11/2012 | Choo et al. |
| 2013/0261584 A1 | 10/2013 | Lee et al. |
| 2013/0261585 A1 | 10/2013 | Lee |
| 2013/0261586 A1 | 10/2013 | Lee et al. |

FOREIGN PATENT DOCUMENTS

| | | |
|---|---|---|
| JP | 2009-112864 A2 | 5/2009 |
| WO | WO 03/086257 A1 | 10/2003 |

* cited by examiner

ABSORBENT ARTICLE WITH HIGHLIGHTED PASSIVE BARRIER

BACKGROUND

The present disclosure relates generally to an absorbent article and more specifically to a feminine care pad having a movable top component.

Absorbent articles such as feminine care products, incontinence products, and training pants are useful to absorb and contain body wastes. These products have developed to the extent that body exudates are quickly drawn and retained away from the wearer's skin so that the wearer remains relatively dry and comfortable. Although this improved performance enhances wearer dryness and comfort, the article can still be subject to leakage, particularly during a fluid insult gush, or when the article is becoming full. In one example, adult care wearers, especially women, are very concerned about leakage in public. Some wearers can be so bothered by leakage that if it occurs in a public place, they will avoid that place and situation for the rest of their life. Leakage is therefore a very undesirable characteristic in an adult care product.

In an attempt to reduce or eliminate the occurrence of leakage, it can be desirable to maintain absorbent articles in close contact with the wearer's body. Such close body fit can allow the absorbent article to absorb body exudates at their source. Achieving close body fit limits the chance for the body exudates to flow off of or out of the absorbent article. However, good body contact might not always be available, particularly along the side regions of an article, which can lead to leakage. Thus, there is a need for an absorbent article that provides close body fit and/or better leak protection, particularly after a fluid insult, without creating undesirable bulk.

SUMMARY

When designing absorbent articles with one or more three-dimensional functional attributes, it is sometimes necessary to highlight certain features to call attention to them, making the consumer aware that there is something unique about the product. Such highlighting, however, should not give the absorbent article the appearance of unreasonable bulk, whether it appears to have too much or too little bulk.

In response to the needs discussed above, a new absorbent article has been developed that will allow women to maintain their active lifestyle with confidence, even on heavy-flow days. In general, the disclosure provides an absorbent article including a barrier that can move in three dimensions, resulting in good body fit and leakage protection.

The top components presented in the disclosure have the ability to conform to the body of the user, including movement in the z-direction, thereby increasing the level of comfort to the user. The structure and arrangement of the top component enables the top component to be moved, taking on a three-dimensional shape, resulting in a closer body fit and increasing the tendency of fluid to be maintained within the pad and reducing the possibility of leakage. In addition, such features can be highlighted in a manner such that the apparent bulk of the article is not seen as being too large or too small.

In some aspects, the absorbent article includes an article body including an absorbent core, a garment-facing surface, a body-facing surface, and a first graphic visible at the body-facing surface; and a top component affixed to the article body at the body-facing surface, wherein the top component includes an attached region and a cantilevered region, and wherein the cantilevered region includes a translucent portion through which the first graphic is at least partially visible.

In other aspects the absorbent article includes an article body including an absorbent core, a garment-facing surface, a body-facing surface, and a first graphic visible at the body-facing surface; and a top component affixed to the article body at the body-facing surface, wherein the top component includes an attached region and a cantilevered region, and wherein the cantilevered region includes a translucent portion through which the first graphic is at least partially visible, wherein the translucent portion of the cantilevered region includes a second graphic, and wherein the first graphic and the second graphic combine to form the appearance of a third graphic.

Numerous other features and advantages of the present disclosure will appear from the following description.

FIGURES

The foregoing and other features and aspects of the present disclosure and the manner of attaining them will become more apparent, and the disclosure itself will be better understood by reference to the following description, appended claims and accompanying drawings, where:

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It should be noted that, when employed in the present disclosure, the terms "includes," "including" and other derivatives from the root term "include" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices that can absorb and contain fluids. For example, personal care absorbent articles refer to devices that are placed against or near the skin to absorb and contain the various fluids discharged from the body. The term includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads such as breast pads, containers, incontinence products, and urinary shields; clothing components; bibs; athletic and recreation products; and the like.

The term "bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

The term "complex liquid" describes a liquid generally characterized as being a viscoelastic liquid including multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like are generally characterized as being relatively low-viscosity and including one or more components having homogeneous physical and/or chemical properties. As a result of having homogeneous properties, the one or more components of simple liquids behave substantially similarly during absorption or adsorption, although some components of the simple liquids can be absorbed or adsorbed more readily than others. Although a complex liquid is generally characterized herein as including specific components having inhomogeneous properties, each specific component of a complex liquid generally has homogeneous properties. Consider, for example, a representative complex body-liquid having three specific components: red blood cells, blood protein molecules and water molecules. Upon examination, one skilled in the art could easily distinguish between each of the three specific components according to their generally heterogeneous properties. Moreover, when examining a particular specific component such as the red blood cell component, one skilled in the art could easily recognize the generally homogeneous properties of the red blood cells.

The term "connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end wearer.

The terms "disposed on," "disposed along," "disposed with," or "disposed toward" and variations thereof are intended to mean that one element can be integral with another element, or that one element can be a separate structure bonded to or placed with or placed near another element.

The term "translucent" generally refers to permitting the passage of light, both in the sense of being transparent, in which objects may be seen clearly therethrough, and in the sense that light may be transmitted and diffused such that objects are not seen clearly therethrough.

These terms can be defined with additional language in the remaining portions of the specification.

The present disclosure incorporates the use of contrasting graphics and material translucency/opacity to control the visual look of an absorbent article in a way that draws the eye to the feature or features the consumer needs to notice. In one example, an absorbent article can incorporate a thin "mini-pad" or top component that can be made from a surge layer and a nonwoven layer and then bonded to the top of an ultra-thin pad or article body. The ultra-thin article body is printed with aesthetically-appealing graphics that that are meant to enhance the use experience but also include a highlight to reinforce to the user that there is adequate leakage protection. For these reasons the top component that is attached must be carefully designed to allow the article body graphics to show, while also calling attention to the fact that there is a new functional feature worth noticing.

The present disclosure adjusts the translucency/opacity of the top component materials to achieve the desired aesthetic balance. If the top component is too opaque, it will look awkward sitting on top of the article body and can make the overall pad look thick and bulky. If the top component is overly sheer, it can look too flimsy and the believability of its functionality will drop.

Absorbent composites of this disclosure are useful in absorbent articles, such as disposable absorbent articles. An absorbent article of the present disclosure can have an absorbent core, and can additionally include a topsheet and/or a backsheet, where the absorbent core can be disposed between the topsheet and the backsheet. The articles can further include leakage top components.

To gain a better understanding of the present disclosure, attention is directed to the figures for exemplary purposes showing a feminine care article of the present disclosure. It is understood that the present disclosure is suitable for use with various other personal care absorbent articles without departing from the scope of the present disclosure.

In one aspect the absorbent article can be a feminine care article such as a feminine care pad or napkin. The article can have a lengthwise, longitudinal direction that can extend along an appointed y-axis of the article, and a transverse, laterally extending, cross direction that can extend along an appointed x-axis of the article. Additionally, the article can include first and second longitudinally opposed end portions, and an intermediate portion located between the end portions. Generally stated, the intermediate portion can be located approximately about the midpoint of an overall, longitudinal length of the article. The feminine care pad also has first and second side edges that are the longitudinal sides of the elongated feminine care pad.

The side edges can be contoured to match the shape of the article. The article can have any desired shape. The feminine care article can, for example, have a dog bone shape, a race track shape, an hourglass shape, a multi-lobal shape, or the like. Additionally, the article can be substantially, longitudinally symmetric, or can be longitudinally asymmetric, as desired.

Figure 1:
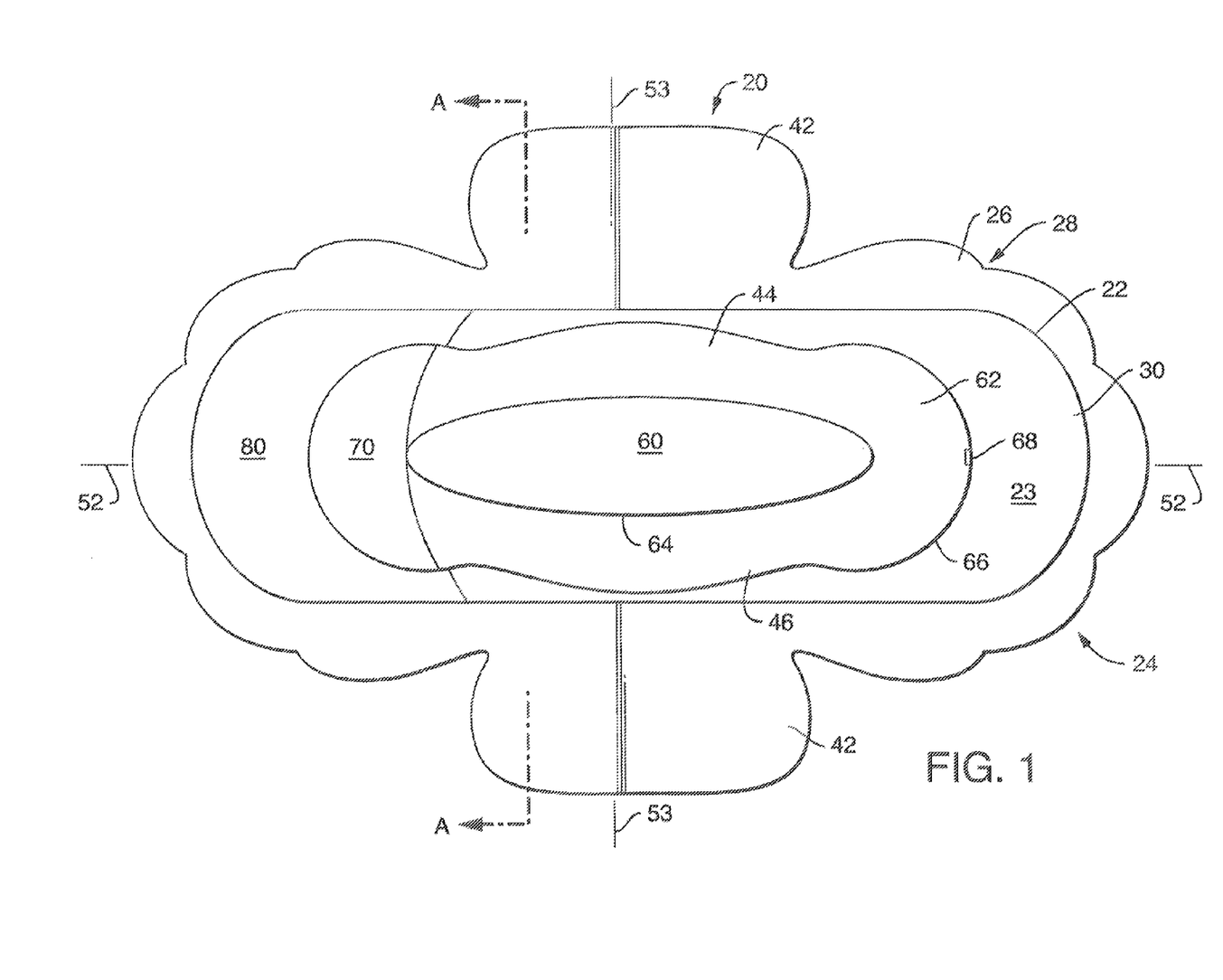
FIG. 1 is a plan view of one aspect of an absorbent article according to the present disclosure.

As representatively shown in FIG. 1, the absorbent article can be a feminine care pad 20 having a longitudinal dimension that is relatively larger than the transverse (lateral) dimension of the article 20. Particular configurations of the absorbent article 20 can include one or more optional body-facing sheet(s) or cover(s) 26 (also referred to as a topsheet) forming at least a portion of the body-facing surface 23 of the article 20, and/or an optional baffle or backsheet 28 forming at least a portion of the garment-facing surface 24 of the article 20. The article 20 has a first major surface that forms a body-facing (bodyside) surface 23 and a second major surface disposed distally from the first major surface that forms a garment-facing surface 24 of the absorbent article 20. In some aspects, a cover 26 is present that can include the first major surface of the absorbent article 20. In some aspects, a backsheet 28 is present that can include the second major surface of the article 20.

Additionally, an absorbent core 30 can be present in the absorbent article 20. In aspects where a cover 26 and backsheet 28 are present, the absorbent core 30 can be positioned between the cover 26 and the backsheet 28. In desired arrangements, the cover 26 can be liquid-permeable, and the backsheet 28 can be operatively liquid-impermeable. In other arrangements, the backsheet 28 can provide an additional permeable outercover of the article 20 positioned over a liquid impermeable layer. As representatively shown, for example, peripheries of the cover 26 and the backsheet 28 can be substantially entirely coterminous. Alternatively, the peripheries of the cover 26 and the backsheet 28 can be partially or entirely non-coterminous.

The cover 26 can include a layer constructed of any operative material, and can be a composite material. For example, the cover layer can include a woven fabric, a nonwoven fabric, a polymer film, a film-fabric laminate, or the like, as well as combinations thereof. Examples of a suitable nonwoven fabric include spunbond fabric, meltblown fabric, coform fabric, carded web, bonded-carded-web, bicomponent spunbond fabric, or the like, as well as combinations thereof. Other examples of suitable materials for constructing the cover layer can include rayon, bonded-carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. In desired arrangements, the cover layer can be configured to be operatively liquid-permeable.

A more particular example of a suitable cover layer material can include a bonded-carded-web composed of polypropylene and polyethylene, such as has been used as a cover stock for KOTEX brand pantiliners. Other examples of suitable materials are composite materials of a polymer and a nonwoven fabric material. The composite materials are typically in the form of integral sheets generally formed by the extrusion of a polymer onto a web of spunbond material. In a desired arrangement, the cover 26 can be configured to be operatively liquid-permeable with regard to the liquids that the article 20 is intended to absorb or otherwise handle. The operative liquid-permeability can, for example, be provided by a plurality of pores, perforations, apertures or other openings, as well as combinations thereof, that are present or formed in the cover layer. The apertures or other openings can help increase the rate at which bodily liquids can move through the thickness of the cover layer and penetrate into the other components of the article 20 (e.g., into the absorbent core 30).

The selected arrangement of liquid-permeability is desirably present at least on an operative portion of the cover 26 that is appointed for placement on the body side of the article 20. The cover 26 can provide comfort and conformability, and can function to direct bodily exudates away from the body and toward the absorbent core 30. In a desired feature, the cover 26 can be configured to retain little or no liquid in its structure, and can be configured to provide a relatively comfortable and non-irritating surface next to the body tissues of a female wearer. The cover 26 can be constructed of any material that is also easily penetrated by bodily fluids that contact the surface of the cover layer.

The cover 26 can also have at least a portion of its bodyside surface treated with a surfactant and/or a menses modifier to increase the surface energy of the material surface or reduce the viscoelastic properties of the menses, and to render the cover 26 more hydrophilic and more wettable to body fluids. The surfactant can permit arriving bodily liquids to more readily penetrate the cover layer. The surfactant can also diminish the likelihood that the arriving bodily fluids, such as menstrual fluid, will flow off the cover layer rather than penetrate through the cover layer into other components of the article 20 (e.g., into the absorbent core structure 30). In a particular configuration, the surfactant can be substantially evenly distributed across at least a portion of the upper, bodyside surface of the cover 26 that overlays the upper, bodyside surface of the absorbent core 30.

The cover 26, if present, can be maintained in secured relation with the absorbent core 30 by bonding all or a portion of the adjacent surfaces to one another. A variety of bonding methods known to one of skill in the art can be used to achieve any such secured relation. Examples of such methods include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover 26 typically extends over the upper, bodyside surface of the absorbent core 30, but can alternatively extend around the article 20 to partially or entirely surround or enclose the absorbent core 30. Alternatively, the cover 26 and the backsheet 28 can have peripheral margins that extend outwardly beyond the terminal, peripheral edges of the absorbent core 30 and the extending margins can be joined to partially, or entirely, surround or enclose the absorbent core 30.

The backsheet 28 can include a layer constructed of any operative material, and can have a selected level of liquid-permeability or liquid-impermeability, as desired. In a particular configuration, the backsheet 28 can be configured to provide an operatively liquid-impermeable backsheet structure. The backsheet 28 can, for example, include a polymeric film, a woven fabric, a nonwoven fabric, or the like, as well as combinations or composites thereof. For example, the backsheet 28 can include a polymer film laminated to a woven or nonwoven fabric. In a particular feature, the polymer film can be composed of polyethylene, polypropylene, polyester, or the like, as well as combinations thereof. Additionally, the polymer film can be micro-embossed. Desirably, the backsheet 28 can operatively permit a sufficient passage of air and moisture vapor out of the article 20, particularly out of an absorbent (e.g., storage or absorbent core 30) while blocking the passage of bodily liquids. An example of a suitable backsheet material can include a breathable, microporous film, such as a HANJIN Breathable Backsheet available from Hanjin Printing, Hanjin P&C Company Limited, Republic of South Korea.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics that have been treated to render them operatively liquid-impermeable. Another suitable backsheet material can include a closed cell polyolefin foam. For example, closed cell polyethylene foam can be employed. Still another example of a backsheet material would be a material that is similar to a polyethylene film that is used on commercially sold KOTEX brand pantiliners.

The structure of the absorbent core 30 can be operatively configured to provide desired levels of liquid retention and storage capacity, and desired levels of liquid acquisition and distribution. More particularly, the absorbent core 30 can be configured to hold a liquid, such as urine, bowel movement, menses, other complex liquid, or the like, as well as combinations thereof. The absorbent core 30 can include a matrix of absorbent fibers and/or absorbent particulate material to form a stabilized structure and the absorbent fiber can include natural and/or synthetic fiber. The absorbent core 30 can also include one or more components that can modify menses or inter-menstrual liquids.

The absorbent core 30 can also include superabsorbent material. Superabsorbent materials suitable for use in the present disclosure are known to those skilled in the art, and can be in any operative form, such as particulate form. Generally stated, the superabsorbent material can be a water-swellable, generally water-insoluble, hydrogel-forming polymeric absorbent material, which is capable of absorbing at least about 10, desirably about 30, and possibly about 60 times or more its weight in physiological saline (e.g., 0.9 wt % NaCl). The hydrogel-forming polymeric absorbent material can be formed from organic hydrogel-forming polymeric material, which can include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking can, for example, be by irradiation or covalent, ionic, Van der Waals, or hydrogen bonding. Suitable materials are available from various commercial vendors, such as Evonik Stockhausen, Inc., a business having offices located in Greensboro, N.C., USA. The superabsorbent material can desirably be included in an appointed storage or retention portion of the absorbent core 30, and can optionally be employed in other components or portions of the absorbent article 20.

The amount of superabsorbent material in a selected layer or other component (e.g., the absorbent core 30) can be at least a minimum of about 1 wt %. The amount of superabsorbent material can alternatively be at least about 5 wt %, and can optionally be at least about 8 wt % to provide improved performance. In other aspects, the amount of superabsorbent material can be up to a maximum of about 75 wt %, or more. The amount of superabsorbent material can alternatively be up to about 35 wt %, and can optionally be up to about 20 wt % to provide improved effectiveness.

If the amount of superabsorbent is outside the desired values, there can be excessive leakage. If the amount of superabsorbent is too high, there can be a poor containment of the superabsorbent gel and an excessive amount of gel on the wearer's skin. Additionally, the transfer of liquid to the shaping layer can be inhibited or the product can have an inadequate rate of liquid intake, causing leakage and excessive wetness against the wearers skin. The manufacturing costs can also become excessive.

In desired configurations, the absorbent core 30 can be configured to provide any operative absorbent capacity. In particular arrangements, for example, the absorbent core 30 can provide a total, overall absorbent saturation capacity of up to about 5 grams of menses stimulant. In other arrangements, the absorbent core 30 can provide a total, overall absorbent saturation capacity that is at least a minimum of about 5.5 grams of menses stimulant. The overall saturation capacity can alternatively be at least about 25 grams, and can optionally be at least about 40 grams of menses stimulant to provide improved performance. In a desired arrangement, the total saturation capacity of the absorbent core 30 can be up to about 107 grams of menses stimulant, or more.

A suitable menses stimulant is composed of swine blood diluted with swine plasma to provide a hematocrit level of 35% (by volume). A suitable device for determining the hematocrit level is a HEMATOSTAT-2 system, available from Separation Technology, Inc., Altamonte Springs, Fla., USA. Alternatively, a substantially equivalent device or system can be employed.

The specific saturation capacity and the specific retention capacity can be determined by soaking a 1 inch by 1 inch (2.54 cm×2.54 cm) sample of absorbent material in an amount of menses stimulant that is sufficient to fully saturate the sample (e.g., 30 mL) for 30 minutes. The wet absorbent is then placed between a layer of through-air-bonded-carded web material and a layer of blotter paper, and a pressure of 0.05 psi (0.345 KPa) is applied for one minute to remove any pools of liquid. The saturated sample is then weighed. The weight of liquid held in the sample divided by the dry weight of the sample is the specific saturation capacity of the sample.

After the saturated sample is weighed, the absorbent sample is placed in a centrifuge and spun at 300 G for three minutes. The spun sample is then weighed. The weight of the liquid remaining in the spun sample divided by the dry weight of the sample is the specific retention capacity of the sample.

Accordingly:

Saturation Capacity=(Wet Wt. Before Centrifuge−Dry Wt.)/(Dry Wt.)

Retention Capacity=(Wet Wt. After Centrifuge−Dry Wt.)/(Dry Wt.)

The total absorbent saturation capacity of an overall layer or other component can be determined by multiplying its specific saturation capacity times the total weight of such component. Similarly, total absorbent retention capacity of an overall layer or other component can be determined by multiplying its specific retention capacity times the total weight of such component.

A suitable through-air-bonded-carded web material has a 2.5 osy (84.8 g/m$^2$) basis weight, a 0.024 g/cm$^3$ density, and is composed of 60 wt % of 6 denier, KoSa type 295 polyester fiber; and 40 wt % of 3 denier, Chisso ESC-HR6 bicomponent fiber. The polyester fiber is available from KoSa, Charlotte, N.C., USA, and the bicomponent fiber is available from Chisso Corporation, Osaka, Japan. A suitable blotter paper is 100-lb white blotter paper. Equivalent materials can optionally be employed.

The absorbent core 30 can be provided by a single unitary layer, or can include a composite structure having a selected plurality of component strata or layers. In some aspects, the absorbent core 30 is desirably a stabilized structure.

In some aspects, the article 20 can include at least one side cover (not shown). Side covers are an additional strip of cover material that is positioned longitudinally along a longitudinal side edge of the article 20 so as to create a dual cover topsheet layer. Side covers are often hydrophobic, but they need not be. Suitable materials for side covers include a fibrous material formed from fusible polymeric fibers or filaments and nonwovens laminated on a film layer. The side cover can be nonperforated, although a perforated web can be used if desired. The side cover can be formed from various polymers, including polyamides, polyesters, polyolefins, polyvinyl acetate, polyvinyl chloride, polyvinyl alcohol, cellulose acetate, viscose, and the like. Suitable materials include polypropylene spunbond and bonded carded webs. In some aspects, the side cover has a uniform web with a denier of about 1.5 or greater. Side covers are also discussed in U.S. Pat. No. 5,415,640, which is incorporated herein by reference in a manner that is consistent herewith.

In some aspects of the disclosure, the article 20 can include a system of side panel or wing portions 42. The side panels 42 can be unitarily formed from a selected component of the article 20, such as the cover 26 and/or the backsheet 28, and are integrally connected to appointed sections of the side regions along the intermediate portion of the article 20. Alternatively, the side panels or wings 42 can be separately provided members that are subsequently attached or otherwise operatively joined to the intermediate portion of the article 20.

The side panels 42 can have an appointed storage position (not shown) in which the side panels 42 are directed generally inwardly toward the longitudinally-extending centerline 52. In some aspects, the side panel 42 that is connected to one side margin can have sufficient cross-directional length to extend and continue past the centerline 52 to approach the laterally opposite side margin of the article 20. The storage position of the side panels 42 can ordinarily represent an arrangement observed when the article 20 is first removed from its wrapper or other packaging. Prior to placing the article 20 into an undergarment prior to use, the side panels 42 can be selectively arranged to extend laterally from the side regions of the article's intermediate portion. After placing the article 20 in the undergarment, the side panels 42 can be operatively wrapped and secured around the side edges of the undergarment to help hold the article 20 in place, in a manner well known in the art.

The side panel portions 42 can have any operative construction and can include a layer of any operative material. Additionally, each side panel 42 can include a composite material. For example, the side panels 42 can include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web, or the like, as well as combinations thereof.

Each side panel 42 can be joined to its corresponding side region of the article 20 in any operative manner. For example, the side panel 42 can be joined to the cover 26, the backsheet 28 or another article component, as well as any combination thereof. As seen in FIG. 1, for example, each side panel 42 is joined to the outward, garment-side surface of the backsheet 28, but can optionally be joined to the bodyside surface of the backsheet 28. The side panel 42 can be attached with hot melt adhesive, but any other operative adhesive or attachment mechanism can alternatively be employed.

In another feature, each side panel portion 42, or any desired combination of the employed side panel portions 42, can include a panel-fastener component (not shown) that is operatively joined to an appointed engagement surface of its associated side panel 42. The panel-fastener component can include a system of interengaging mechanical fasteners, a system of adhesive fasteners, or the like, as well as combinations thereof.

In certain aspects each side panel 42 can include a cooperating component of an interengaging mechanical fastener system. The component can be a "male" component (e.g., a hook component) of the fastener system. Any operative hook component can be employed. For example, a suitable hook component material can include a J-hook, mushroom-head hook, flat-top nail-head hook, a palm-tree hook, a multiple-J hook, or the like, as well as combinations thereof. Alternatively, either or both side panels 42 can include a panel-fastener system that incorporates an operative adhesive. The adhesive can be a solvent-base adhesive, a hot melt adhesive, a pressure-sensitive adhesive, or the like, as well as combinations thereof.

An operative first section of the selected hook component can be joined to a major facing surface of at least a first side panel portion 42 and can be configured to contact or otherwise engage a second side panel portion 42 during ordinary use. Additionally, an operative second section of a hook component, composed of the same or different type of hook material, can be joined to a major facing surface of the second side panel portion 42 and can be configured to contact or otherwise engage an outward surface of the wearers undergarment during ordinary use. For example, the hook component can be arranged to operatively engage and removably attach to the outward surface of a crotch region of the undergarment.

Each side panel portion 42, or any desired combination of the employed side panel portions 42, can include a loop or other "female" component of an interengaging mechanical fastener system. Any operative loop component can be employed. For example, a suitable loop component material can include a woven fabric, a knit fabric, a nonwoven fabric, a fabric laminated to a substrate, or the like, as well as combinations thereof.

An operative first section of a selected loop component can be joined to a major facing surface of at least the second side panel portion 42 and can be configured to contact or otherwise engage the hook component on the first side panel portion 42 during ordinary use. Additionally, an operative second section of a loop component, composed of the same or different type of loop material, can be joined to a major facing surface of the first side panel portion 42. As a result, the user can have the option of alternatively attaching the second hook component of the second side panel 42 onto the second loop component of the first side panel 42. Accordingly, the hook component can alternatively be engaged with the outward surface of the wearers undergarment.

Each or any desired combination of the provided loop components can be a separately provided member that is subsequently joined and assembled to its corresponding side panel portion 42. In a desired feature, each or any desired combination of the provided loop components can be integrally provided by the material employed to construct its corresponding side panel portion 42.

In the various arrangements of the present disclosure, the hook component can be configured to have a particularly selected hook concentration or density (hooks per unit area). In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$) and can optionally be at least about 3000 hooks/in$^2$ (about 465 hooks/cm$^2$) to provide improved performance. In another aspect, the hook density cannot exceed about 7000 hooks/in$^2$ (about 1085 hooks/cm$^2$). The hook density can alternatively not exceed about 6000 hooks/in$^2$ (about 930 hooks/cm$^2$) and can optionally not exceed about 5000 hooks/in$^2$ (about 775 hooks/cm$^2$) to provide improved performance.

Examples of suitable hook materials can include 85-Series and 61-Series hook materials available from Velcro, USA, Manchester, N.H. The hook materials can have a hook density of about 775 hooks/cm$^2$.

In a particular aspect, the material of the loop component can include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web can include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515, the entire disclosure of which is hereby incorporated by reference in a manner that is consistent herewith.

The complementary components of the mechanical fastener are configured to provide a selected attachment peel-force value. In a particular aspect, the peel-force value can be at least a minimum of about 75 grams (g). The peel-force value can alternatively be at least about 100 g and can optionally be at least about 150 g to provide improved performance. In other aspects, the peel-force value can be up to a maximum of about 300 g, or more. The peel-force value can alternatively be up to about 250 g and can optionally be up to about 225 g to provide improved effectiveness.

The complementary components of the mechanical fastener are also configured to provide a selected attachment shear-force value. In a particular aspect, the shear-force value can be at least a minimum of about 1000 g. The shear-force value can alternatively be at least about 1250 g and can optionally be at least about 1500 g to provide improved performance. In other aspects, the shear-force value can be up to a maximum of about 3500 g, or more. The shear-force value can alternatively be up to about 3000 g and can optionally be up to about 2000 g to provide improved effectiveness.

If the peel-force and/or the shear-force are outside the desired values, the fasteners can experience premature unfastening, or can be too difficult to unfasten to remove the article 20 from an associated undergarment.

In the construction of the article 20, the various components can be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

The article 20 of the present disclosure includes at least one top component 44. The top component 44 serves to establish a barrier to leakage from the article 20, such as side leakage for example, and can help keep the body-facing surface 23 of the feminine care article 20 and the underlying absorbent material in close proximity to the wearer's body. The top component 44 can be provided in a number of forms, including as a separate structure or as an integrated structure. By integrated structure, it is meant that the top component 44 is located within the article body 22, rather than being attached as an isolated component to the body-facing surface 23 of the absorbent article 20.

In one aspect of the disclosure, the feminine care pad or article 20 shown in FIG. 1 is provided with a flat top component 44. If the top component 44 has a radius of curvature, then the radius of curvature toward the wearer's body can be, for example, about 5 mm. However, in some desirable aspects, the top component 44 is relatively flat so as not to draw the attention of the wearer when preparing for use. If the top component 44 is flat, then the radius of curvature is effectively zero.

The top component 44 can have any shape that is desired. For example, in one aspect, the top component 44 has an oval shape, such as illustrated in FIG. 1. The top component 44 in this aspect is defined by a continuous peripheral edge 46, a longitudinally-extending centerline 52 and transversely-extending centerline 53. In the aspect illustrated in FIG. 1, the top component 44 is symmetrical about both the transversely- and longitudinally-extending centerlines 53, 52, but it need not be.

The top component 44 can be of any caliper. However, in some desirable aspects, the caliper of the top component 44 is less than or equal to about 1.5 mm, more preferably less than about 1 mm or less, so that the total caliper of the feminine care pad 20 is less than about 4 mm, such as less than about 3 mm. It is understood, however, that a thicker top component 44 and/or thicker article body 22 can also be provided within the scope of the disclosure.

The top component 44 can be any length as desired and can be dependent on the size of the article 20. In a preferred aspect the top component 44 has a length that is in proportion to the length of the article 20. In certain aspects the length of the top component 44 can range in length from about 25 to about 270 mm, such as from about 50 to about 200 mm to provide improved performance. In one particular aspect, the length of the top component 44 is about 170 mm.

The top component 44 also has a width dimension. The top component 44 can be any width desired, and can be dependent on the size of the article 20. For example, the top component 44 can range in width from about 5 to about 80 mm, such as from about 30 to about 60 mm to provide improved performance. In one particular aspect, the width of the top component 44 is about 55 mm.

In general, the top component 44 should be flexible enough so that the absorbent article 20 is comfortable to wear.

The top component 44 is preferably liquid pervious and absorbent. Thus, in one aspect of the present disclosure, when the top component 44 is absorbent, it can provide additional absorbent capacity in the article 20. The top component 44 can be formed from many types of materials. For example, the top component 44 can be formed from soft flexible material such as foam, fluff, paper, nonwoven or the like. For instance, absorbent material such as webs or laminates of absorbent material, with or without superabsorbent materials, can be suitable. Examples of suitable absorbent materials also include webs of cross-linked cellulosic fibers and meltblown webs.

Figure 2:
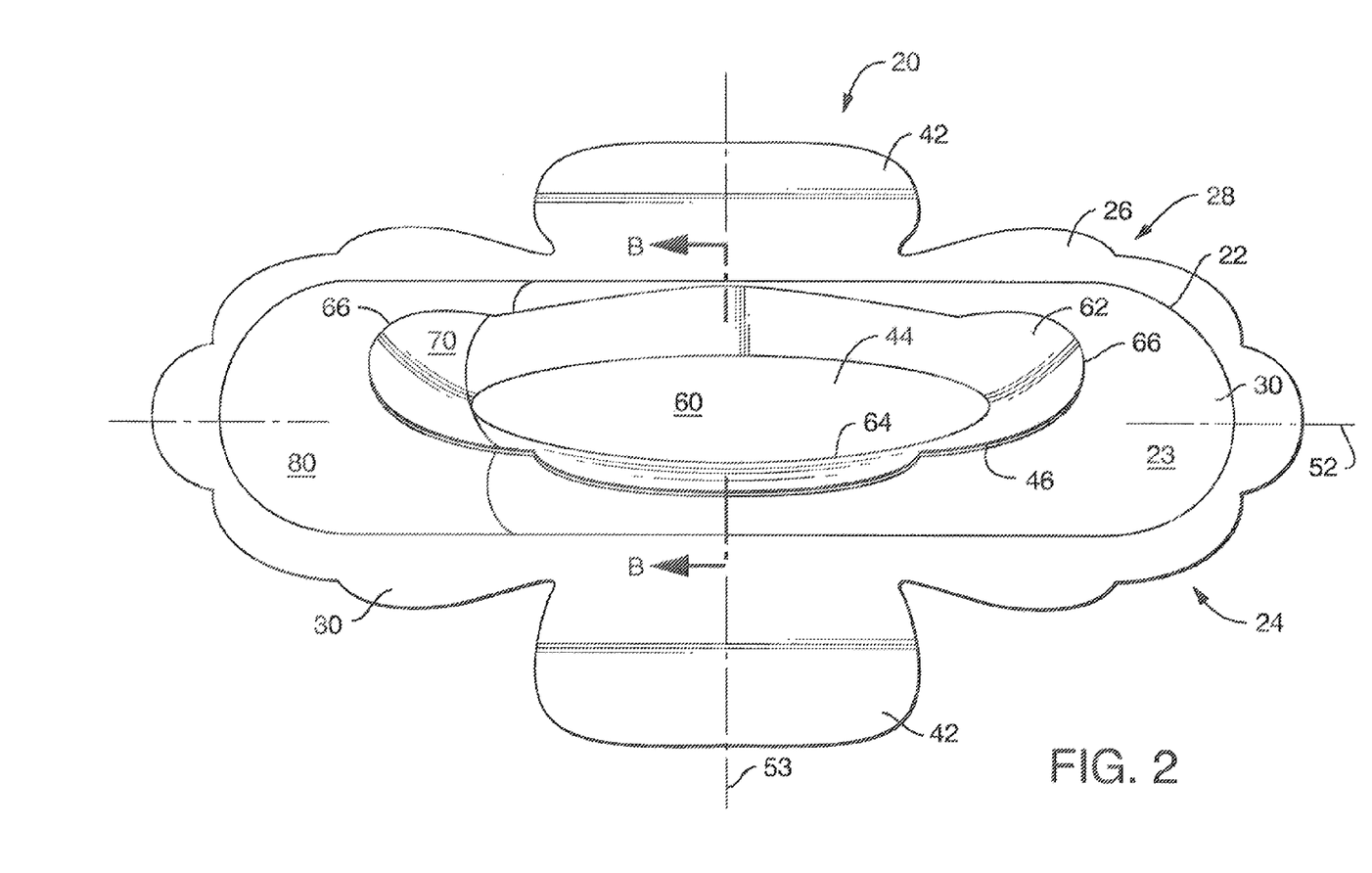
FIG. 2 is a perspective view of the absorbent article of FIG. 1.
Figure 3:
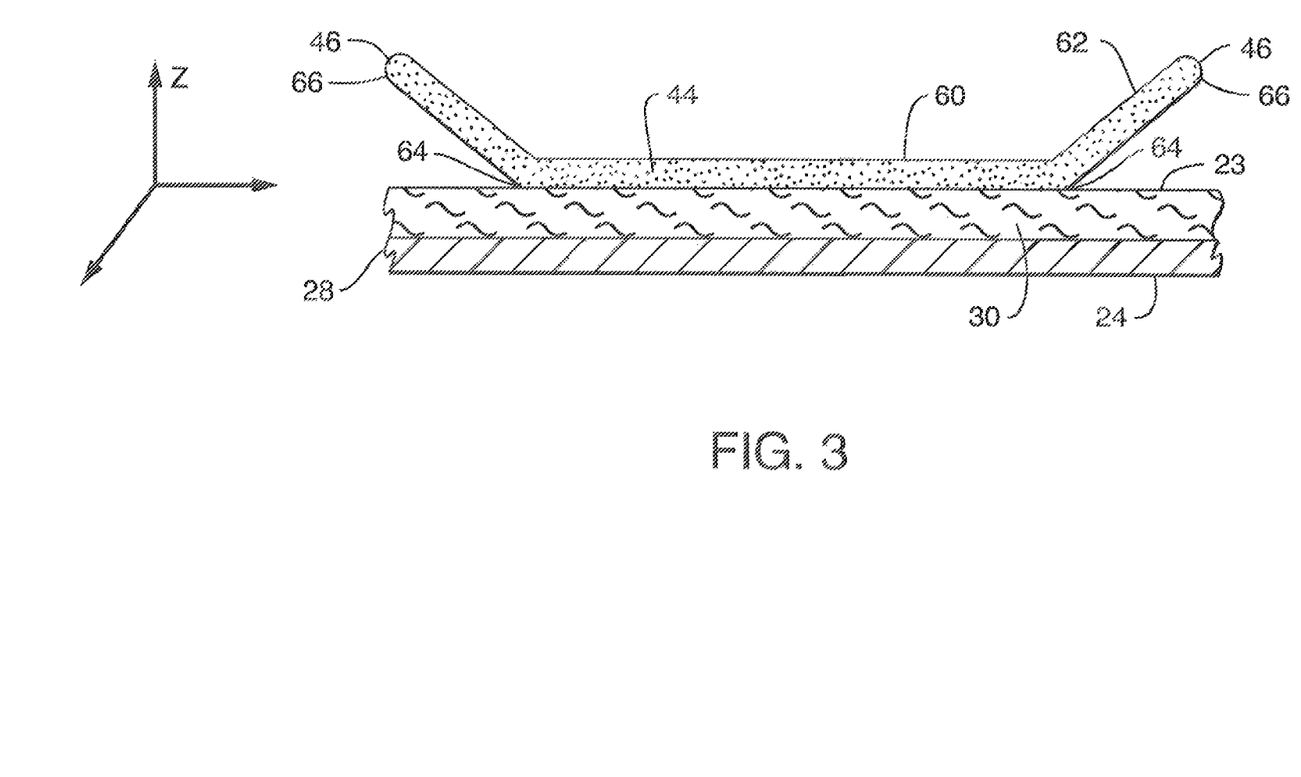
FIG. 3 is a cross sectional view of the absorbent article of FIG. 2 through the line B-B.
Figure 4:
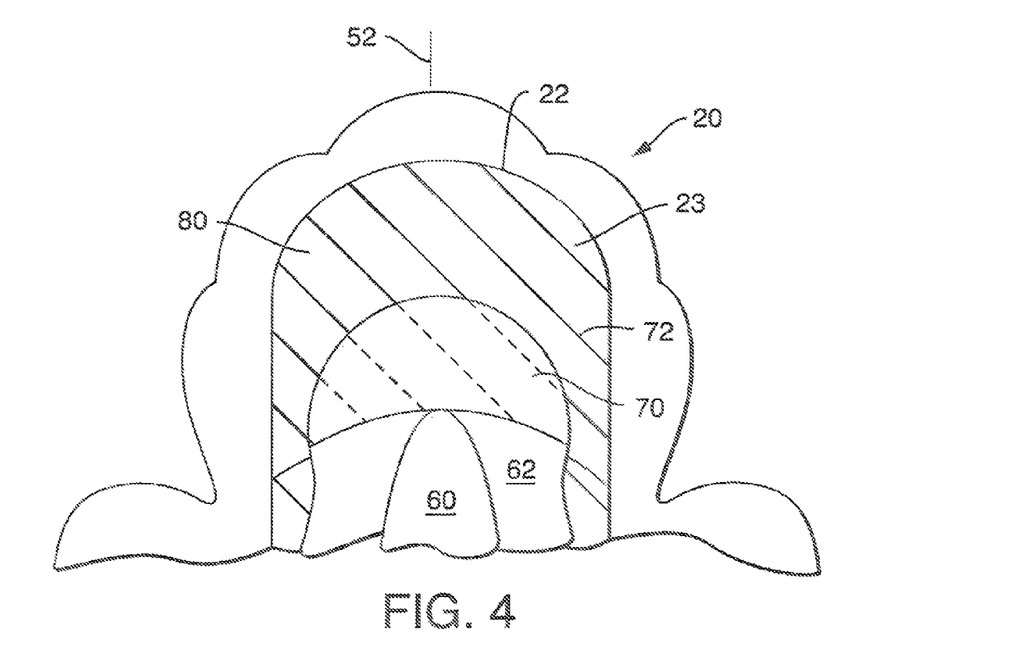
FIG. 4 is a partial plan view of the absorbent article of FIG. 1 taken from the line A-A and illustrating one aspect of the present disclosure.
Figure 5:
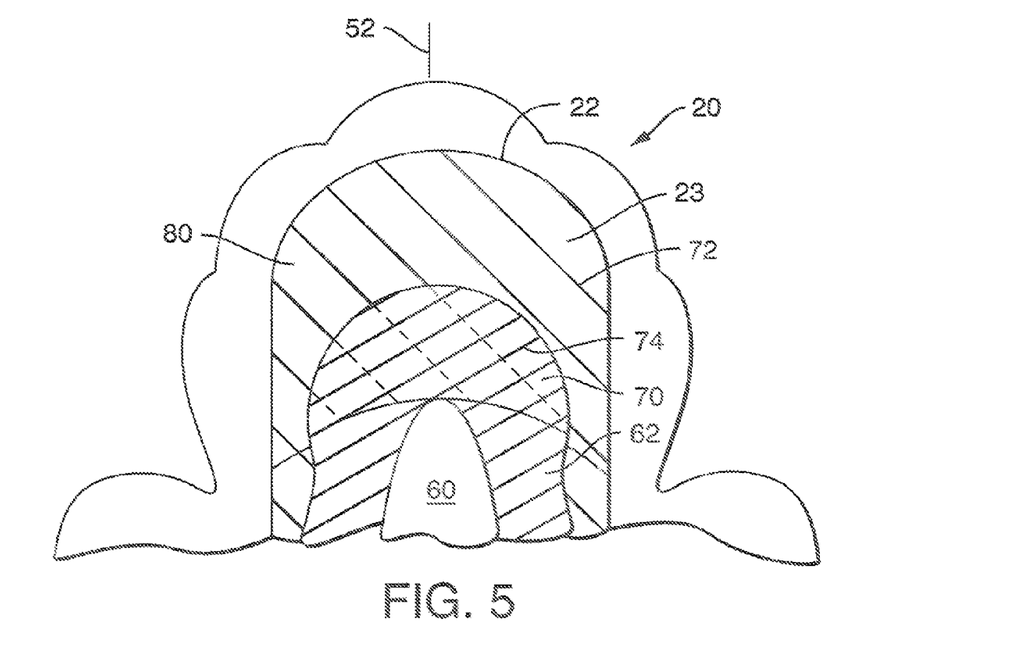
FIG. 5 is a partial plan view of the absorbent article of FIG. 1 taken from the line A-A and illustrating another aspect of the present disclosure.

Generally, the top component 44 is attached to the article body 22 and preferably to the body-facing side of the cover 26 (if present). In still other aspects, the top component 44 is attached to one of the various other layers or components of the article body 20, such as the absorbent core 30 for example. Attachment of the top component 44 to the article 20 defines an attached region 60 and a cantilevered region 62. The attached region 60 is bordered by a perimeter 64, and the cantilevered region 62 extends from the perimeter 64. In one aspect, the cantilevered region 62 is attached to the top component 44 and to the article body 20 only at the perimeter 64, leaving a free edge 66 in the cantilevered region 62 opposite the perimeter 64. In other aspects, a portion of the free edge 66 can be attached to the article body 20 at an attachment point 68. The portion of the cantilevered region 62 immediately between the perimeter 64 and the attachment point 68 can be attached or unattached to the article body 22. The cantilevered region 62 is generally hingedly movable at the perimeter 64. The cantilevered region 62 can be biased such that it spaces apart from the article body 22 during manufacture, during use, or at any other suitable points. A method for such biasing includes curves in the top component 44, perimeter 64, or free edge 66, or any other suitable arrangement. A spaced-apart cantilevered region 62 is illustrated in FIGS. 2 and 3.

In another aspect of the present disclosure, the cantilevered region 62 can include a translucent portion 70 such that light can pass through that portion of the cantilevered region 62. The translucent portion 70 can be configured such that any first graphics 72 (see FIGS. 4-7) or other feature disposed on the article body 22 below the translucent portion 70 (and that would normally be hidden by the cantilevered region 62) can be at least partially seen through the cantilevered region 62, thus becoming visible at the body-facing surface 23. Graphics are not illustrated in FIGS. 1-3 for clarity purposes. In other aspects, the entire cantilevered region 62 can be translucent. In still other aspects, different portions of the cantilevered region 62 can have different magnitudes of translucency.

The properties of the translucent portion 70 can be selected to exhibit different effects, particularly in the appearance and/or visibility of a first graphic 72 or other feature on the article body 22 beneath the translucent portion 70. For example, the translucent portion 70 can be colored, polarized, or can include a second graphic 74 (see FIGS. 5 and 7) or other feature different from that on the article body 22 beneath the translucent portion 70. In these aspects, the appearance of the first graphic 72 or other feature on the article body 22 beneath the translucent portion 70 will be altered or affected by the translucent portion 70. In a particular aspect, a second graphic 74 on the translucent portion 70 can be disposed such that it visually interacts with the first graphic 72 or other feature on the article body 22 beneath the translucent portion 70 to form a third graphic 76 (see FIG. 5).

The interaction between the first graphic 72 and the translucent portion 70 (and optionally the second graphic 74) creates a highlight on the top component 44. The first graphic 72 can be registered with the second graphic 74 such that the third graphic 76 is a highlight focusing a user's attention on a feature of the article 20. By using a single graphical pattern on a single material that is not the top component 44, there can appear a second graphical pattern that is perfectly registered to the single graphical pattern, thereby creating the appearance of a highlight on the top component 44.

Figure 6:
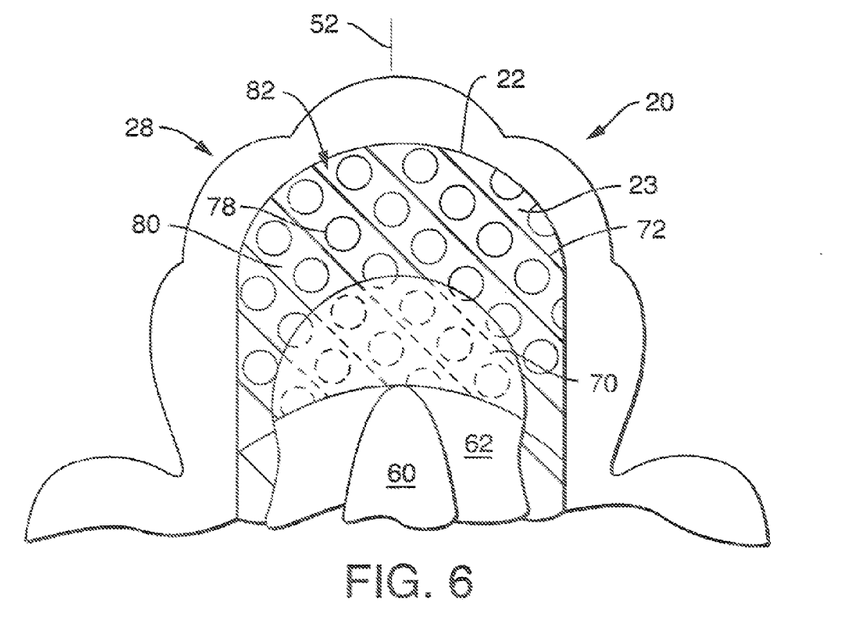
FIG. 6 is a partial plan view of the absorbent article of FIG. 1 taken from the line A-A and illustrating still another aspect of the present disclosure.
Figure 7:
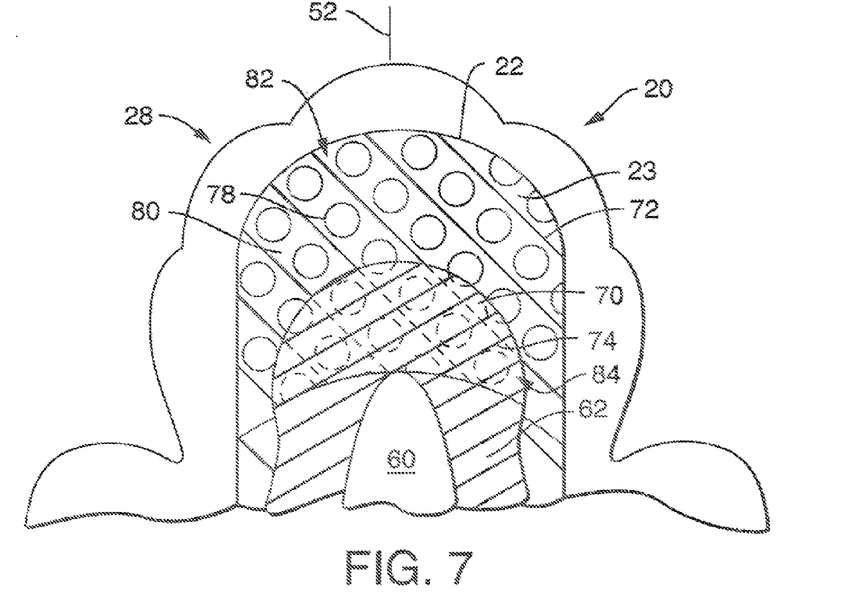
FIG. 7 is a partial plan view of the absorbent article of FIG. 1 taken from the line A-A and illustrating yet another aspect of the present disclosure.

In another aspect of the present disclosure, the baffle 28 includes a baffle graphic 78 or other feature (see FIGS. 6 and 7). In addition, at least a section of the article body 22 can be translucent such that the baffle graphic 78 is visible at the body-facing surface 23. The translucent section 80 can be configured such that any baffle graphics 78 or other feature disposed on the baffle 28 below the translucent section 80 (and that would normally be hidden by the article body 22) can be at least partially seen through the article body 22, thus becoming visible at the body-facing surface 23. In other aspects, the entire article body 22 can be translucent. In still other aspects, different sections of the article body 22 can have different magnitudes of translucency.

The properties of the translucent section 80 can be selected to exhibit different effects, particularly in the appearance and/or visibility of a baffle graphic 78 or other feature on the baffle 28 beneath the translucent section 80. For example, the translucent section 80 can be colored, polarized, or can include a first graphic 72 or other feature different from that on the baffle 28 beneath the translucent section 80. In these aspects, the appearance of the baffle graphic 78 or other feature on the baffle 28 beneath the translucent section 80 will be altered or affected by the translucent section 80. In a particular aspect, a first graphic 72 on the translucent section 80 can be disposed such that it visually interacts with the baffle graphic 78 or other feature on the baffle 28 beneath the translucent section 80 to form the appearance of a fourth graphic 82 (see FIG. 6).

In various combinations of these aspects, the translucent portion 70 of the cantilevered region 62 can include a second graphic 74, the translucent section 80 of the article body 22 can include a first graphic 72, and the baffle 28 can include a baffle graphic 78. In this aspect, the first, second, and baffle graphics 72, 74, 78 can combine to form the appearance of a fifth graphic 84 (see FIG. 7).

At least one top component 44 can be located in any desired location on the article 20. Preferably, the top component 44 is located on the transverse centerline 53 and/or on the longitudinal centerline 52, such as seen in FIG. 1. In other aspects, at least one top component 44 can be disposed at various other locations on the article 20, such as oriented in the transverse-extending direction located a distance from one side or another side of the transverse-extending centerline 53 of the article 20, or in a diagonal direction, or any other suitable orientation as desired.

In still other aspects the movement of the periphery of the top component 44 can be facilitated by one or more movement-enhancing elements. Movement-enhancing elements can include, without limitation, embossing and perforations. Movement-enhancing elements can also include adhering the top component 44 and the cover 26 with varying adhesive patterns and degrees of adhesion. Without being bound by any particular theory, it is believed that embossing the top component 44 controls the level of rise of the peripheral regions of the absorbent layer when the regions are engaged by mechanical forces. Further, the embossing pattern can be continuous, disjointed, straight, or arched and can also vary in the width and depth of embossing, or can be a combination of the above. In addition to performing the control function, the embossing pattern can also serve as a barrier to fluid flow by increasing the difficulty of fluid passage across the pattern.

While the disclosure has been described in detail with respect to specific aspects thereof, it will be appreciated that those skilled in the art, upon attaining understanding of the foregoing will readily appreciate alterations to, variations of, and equivalents to these aspects. Accordingly, the scope of the present disclosure should be assessed as that of the appended claims and any equivalents thereto. Additionally, all combinations and/or sub-combinations of the disclosed aspects, ranges, examples, and alternatives are also contemplated.

The invention claimed is:

1. An absorbent article comprising:
    an article body including an absorbent core, a garment-facing surface, a body-facing surface, and a first graphic visible at the body-facing surface; and
    a top component affixed to the article body at the body-facing surface, wherein the top component includes an absorbent material, and wherein the top component includes an attached region and a cantilevered region, and wherein the cantilevered region includes a translucent portion through which the first graphic is at least partially visible.

2. The absorbent article of claim 1, wherein the translucent portion is configured to alter the appearance of the first graphic.

3. The absorbent article of claim 1, wherein the entire cantilevered region is translucent.

4. The absorbent article of claim 1, wherein the translucent portion of the cantilevered region includes a second graphic.

5. The absorbent article of claim 4, wherein the first graphic and the second graphic combine to form the appearance of a third graphic.

6. The absorbent article of claim 1, wherein the attached region has a perimeter, and wherein the cantilevered region extends from the perimeter.

7. The absorbent article of claim 6, wherein the cantilevered region is configured to be hingedly movable at the perimeter.

8. The absorbent article of claim 6, wherein a portion of the cantilevered region apart from the perimeter is attached to the article body.

9. The absorbent article of claim 1, wherein the cantilevered region includes a plurality of layers.

10. The absorbent article of claim 1, wherein the cantilevered region is configured to be spaced apart from the body-facing surface.

11. The absorbent article of claim 1, wherein the article body includes a baffle forming at least part of the garment-facing surface, and wherein the baffle includes a baffle graphic.

12. The absorbent article of claim 11, wherein at least a portion of the article body is translucent such that the baffle graphic is visible at the body-facing surface.

13. The absorbent article of claim 12, wherein the first graphic and the baffle graphic combine to form the appearance of a fourth graphic.

14. The absorbent article of claim 12, wherein the cantilevered region includes a second graphic, and wherein the first graphic, the baffle graphic, and the second graphic combine to form the appearance of a fifth graphic.

15. An absorbent article comprising:
   an article, body including an absorbent core, a garment-facing surface, a body-facing surface, and a first graphic visible, at the body-facing surface; and
   a top component affixed to the article body at the body-facing surface, wherein the top component includes an absorbent material, and wherein the top component includes an attached region and a cantilevered region, and wherein the cantilevered region includes a translucent portion through which the first graphic is at least partially visible, wherein the translucent portion of the cantilevered region includes a second graphic, and wherein the first graphic and the second graphic combine to form the appearance of a third graphic.

16. The absorbent article of claim 15, wherein the attached region has a perimeter, and wherein the cantilevered region extends from the perimeter.

17. The absorbent article of claim 16, wherein the cantilevered region is configured to be hingedly movable at the perimeter.

18. The absorbent article of claim 16, wherein a portion of the cantilevered region apart from the perimeter is attached to the article body.

19. The absorbent article of claim 15, wherein the cantilevered region includes a plurality of layers.

* * * * *